(12) United States Patent
Colclough et al.

(10) Patent No.: US 6,673,921 B2
(45) Date of Patent: Jan. 6, 2004

(54) CHEMICAL PROCESS

(75) Inventors: David Colclough, Kent (GB); Anne Hodgson, Kent (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/240,905

(22) PCT Filed: Apr. 4, 2001

(86) PCT No.: PCT/EP01/03820

§ 371 (c)(1),
(2), (4) Date: Feb. 19, 2003

(87) PCT Pub. No.: WO01/77143

PCT Pub. Date: Oct. 18, 2001

(65) Prior Publication Data

US 2003/0158082 A1 Aug. 21, 2003

(30) Foreign Application Priority Data

Apr. 5, 2000 (GB) .............................................. 0008179

(51) Int. Cl.$^7$ ............................................ C07D 243/12
(52) U.S. Cl. ...................................................... 540/518
(58) Field of Search ......................................... 540/518

(56) References Cited

FOREIGN PATENT DOCUMENTS

| EP | 0 376 849 | 7/1990 |
|----|-----------|--------|
| EP | 0 728 748 | 8/1996 |
| WO | 94/25445  | 11/1994 |
| WO | 94/40655  | 12/1994 |

*Primary Examiner*—Bruck Kifle
(74) *Attorney, Agent, or Firm*—Bonnie L. Deppenbrock

(57) ABSTRACT

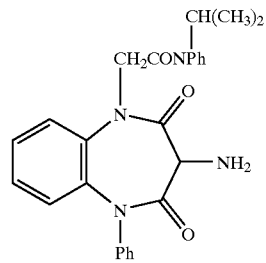

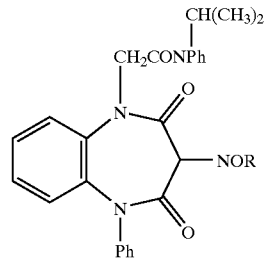

A process for the preparation of the compound (I) or an acid addition salt thereof which comprises reacting a compound of formula (II), wherein R is an optionally substituted benzyl group under concomitant reduction and hydrogenolysis conditions, followed, if required, by isolation of the compound as an acid addition salt thereof.

6 Claims, No Drawings

CHEMICAL PROCESS

This application is filed pursuant to 35 U.S.C. §371 as a United States National Phase Application of International Application No. PCT/EP01/03820 filed Apr. 4, 2001, which claims priority from GB 0008179.4 filed Apr. 5, 2000.

The present invention relates to an improved process for preparing an intermediate for use in the synthesis of Cholecystokinin (CCK) agonists.

WO94/24149 describes a class of 1,5-benzodiazepine derivatives having an agonist action at the CCK-A receptor.

A particular interesting group of 1,5-benzodiazepine derivatives described therein may be represented by the general formula (A)

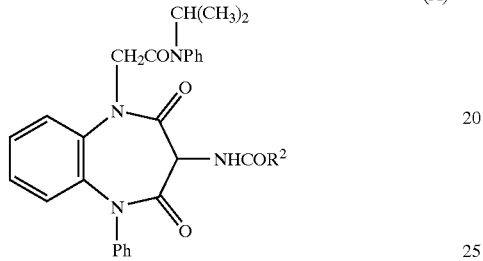

(A)

The compounds of formula A are conveniently prepared from the 3-amino derivative (I).

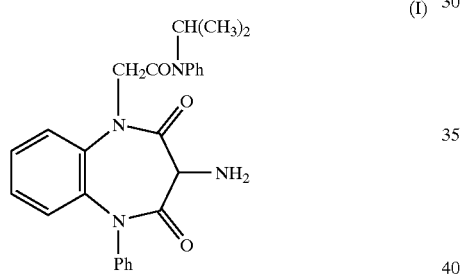

(I)

WO94/24149 teaches that such 3-amino-1,5-benzodiazepine derivatives may be prepared by reduction of the corresponding phenylhydrazone and the preparation of the compound of formula (I) by the reduction of the corresponding phenylhydrazone (B), is specifically described in intermediate 11 therein.

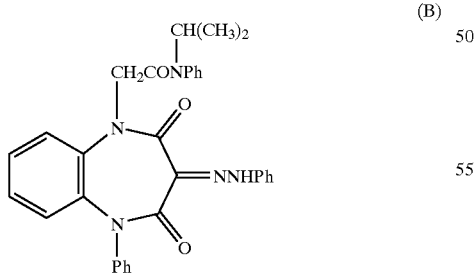

(B)

Reduction of the hydrazone (B) to give the amine (I) also results in the formation of aniline. This is a highly toxic product, the generation of which should be avoided if at all possible in a commercial process and thus there is a need to find an alternative synthesis to the primary amine (I) which avoids the generation of aniline and provides the required product in good yield.

We have now found that the required amine (I) can be prepared in high yield and without the consequential generation of toxic by products by concomitant reduction and hydrogenolysis of the corresponding oxime (II), wherein R is an optionally substituted benzyl group.

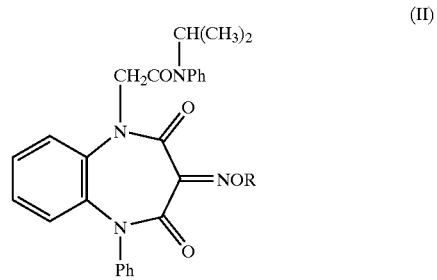

(II)

Thus the present invention provides for a process for preparing the amine (I) by concomitant reduction and hydrogenolysis of the oxime (II) followed, if desired, by isolation of the compound as an acid addition salt thereof.

The concomitant reduction and hydrogenolysis is conveniently carried out using a Palladium catalyst e.g. Palladium on charcoal catalyst in the presence of hydrogen or ammonium formate in a solvent such as an alkanol e.g. ethanol, isopropanol or an aqueous ethanol, e.g. aqueous ethanol, or tetrahydrofuran For the reaction the group R is conveniently benzyl or a substituted benzyl group e.g. p-methoxybenzyl or benzhydryl. Preferably R is benzyl The oxime (II) may conveniently be prepared by reaction of the ortho-phenylene diamine derivative (III)

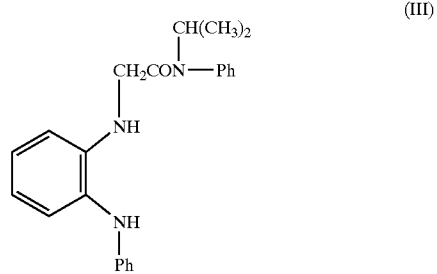

(III)

with an activated derivative of the di-acid (IV), wherein R is an optionally substituted benzyl group.

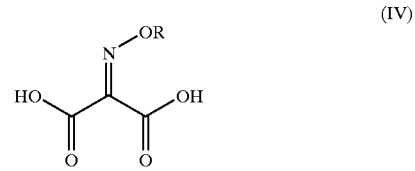

(IV)

Conveniently, the activated derivative of the di acid (IV) is the corresponding diacylhalide e.g. chloride and this is prepared in situ by reaction of the di-acid (IV) with an oxalyl halide e.g. oxalyl chloride. The reaction is conveniently carried out in an aprotic solvent such as an ester e.g. ethyl acetate, dichloromethane, toluene, or dimethoxyether or mixtures thereof, and in the presence of dimethylformamide.

The di acid (IV) is conveniently prepared by reaction of a dialkyl ketomalonate e.g. diethyl ketomalonate with the corresponding hydroxylamine derivative $RONH_2$ in a solvent such as an alkanol or industrial methylated spirits and in the presence of a base e.g. pyridine, or sodium hydroxide followed, if required, by reaction with aqueous sodium hydroxide.

The following examples, which are non-limiting, illustrate the invention.

In the Examples the abbreviations EtOAc=ethyl acetate; MeOH=methanol, DMF=N,N-dimethylformamide; IPA=isopropyl alcohol; IMS=industrial methylated spirits.

Intermediate 1

Diethyl 2-[(benzyloxy)imino]malonate

Di-ethylketomalonate (60 g) was added at 20° C. to a stirred suspension of O-benzylhydroxylamine (57.8 g) in IMS (500 ml) containing pyridine (30 ml). The reaction was heated at 75° C. for 4 hr. The reaction was cooled and solvents removed under reduced pressure. The residue was partitioned between EtOAc (500 ml) and water (300 ml) and the organic layer separated, washed with water (250 ml) and dried over $MgSO_4$. Solvents were evaporated to give the title compound 95.3 g, as a colourless oil (99% th, ca 3% w/w residual EtOAc) which was used without further purification.

1H NMR (300 MHz, $CDCl_3$) 7.4 (m, 5H), 5.35 (s, 2H), 4.35 (m, 4H), 1.3 (m, 6H).

Intermediate 2

Method A

2-[(benzyloxy)imino]malonic acid

To a solution of Intermediate 1 (40 g) in MeOH (80 ml) was added 2M NaOH (200 ml) over 20 mins. The reaction was stirred at room temperature for 2 hr. MeOH was removed under reduced pressure and the residual solution was acidified to pH 2 by dropwise addition of conc.HCl (~30 ml) while cooling to maintain the temperature below 35° C. A thick white slurry was formed which was diluted with water (50 ml) to aid mobility. The solids were collected by filtration, washed with chilled water (25 ml) and dried in vacuo at 55° C. to give the title compound as a white solid (17 g) found to contain ca.10% w/w residual inorganic salts. Corrected yield ~45% th. Used without further purification.

1H NMR (300 MHz, $D_2O$) 7.4 (m, 5H), 5.2 (s, 2H)

Method B

2-[(Benzyloxy)imino]malonic acid

To a solution of sodium hydroxide (5.74 g) in water (50 ml) and IMS (80 ml) was added benzylhydroxylamine hydrochloride (22.9 g). Diethyl ketomalonate (25 g,) was added and the mixture warmed to 60° C. and stirred for 4 h. The mixture was cooled to 30° C. and then added over ~10 minutes to a solution of sodium hydroxide (16.1 g) in water (180 ml) maintaining the internal temperature between 25–30° C. The mixture was stirred at 25° C. for ~1 h. This solution was added to a mixture of conc. hydrochloric acid (50 ml) in ethyl acetate (160 ml) and water (20 ml) at 10° C. The rate of addition is controlled to maintain the internal temperature below 15° C. The mixture was allowed to warm to 25° C., and the phases were separated. The aqueous phase was extracted with ethyl acetate (200 ml) and this wash was combined with the organic phase. The solution was concentrated to ~100 ml by distillation under reduced pressure. Toluene (50 ml) was added and the mixture concentrated under reduced pressure to ~100 ml. Further toluene (150 ml) was added and the mixture concentrated under reduced pressure to ~100 ml and precipitation of a white solid was observed. The solid was collected by filtration and washed with toluene. The solid was dried in vacuo at 40° C. to give the title compound (24.4 g).

Intermediate 3

2-[-3-[(Benzyloxy)imino]-2,4-dioxo-5-phenyl-2,3,4,5-tetrahydro-1H-1,5-benzodiazepinyl)-N-isopropyl-N-phenylacetamide Method A Oxalyl chloride (38.3 g) was added dropwise (~1 hr) to a stirred suspension of Intermediate 2 (40 g, corrected for salt content to 31.4 g) in EtOAc (200 ml) containing DMF (0.5 ml, 5 mol %). The mixture was stirred at 25° C. for 0.5 hour then filtered through a pad of Dicalite, washing with EtOAc (40 ml) to give a clear yellow solution. The solution was added (~5 mins) to a stirred slurry of N-isopropyl-N-phenyl-2-(2-phenylaminophenylamino)-acetamide (50 g) in EtOAc (120 ml) at 25° C. The mixture was warmed to 60° C. and a dark purple solution formed. After 1 hr, EtOAc (200 ml) was removed by atmospheric distillation. IPA (120 ml) and water (40 ml) were added and the mixture distilled further to remove more solvent (80 ml). IPA (40 ml) and water (40 ml) were added and a further amount of solvent was distilled out (80 ml). The reaction mixture was cooled to 25° C. over 1.5 hr and the solids collected by filtration. The solids were washed with IPA (2×120 ml), water (1×120 ml) and finally IPA again (1×40 ml) then dried in vacuo at 55° C. to give the title compound as a powder (56.6 g).

1H NMR (300 MHz, $CDCl_3$) 2:1 mixture of isomers about the oxime 7.6–6.95 (m. 18H), 6.9 (t 1H), 5.3 (m, 2H), 4.95 (m, H), 4.65 (d, 0.33H), 4.4 (d, 0.67H), 4.1 (d, 0.67H), 4.0 (d, 0.33H), 0.95 (m, 6H)

Method B

Oxalyl chloride (143 g) was added dropwise over ~1 h to a stirred solution of 2-[(benzyloxy)imino]malonic acid (123 g) in ethyl acetate (250 ml) containing N,N-dimethylformamide (1.2 g) at 25° C. The homogeneous mixture was stirred for 2 hr. The solution was added over ~1 h to a stirred slurry of N-isopropyl-N-phenyl-2-(2-phenylamino)-acetamide (198 g) in ethyl acetate (800 ml) at 60° C. The reaction mixture was stirred at 60° C. for at least 1.5 h. The mixture (suspension) was cooled to 30° C. and isopropanol (200 ml) was added and the suspension stirred overnight. The solid was collected by filtration, washing with isopropanol and dried at 55° C. in vacuo to yield the title compound as a pale yellow solid (187 g).

EXAMPLE 1

(±)-2-(3-Amino-2,4-dioxo-5-phenyl-2,3,4,5-tetrahydrobenzo-[b][1,4]diazepen-1-yl)-N-isopropyl-N-phenylacetamide Method A To a stirred suspension of Intermediate 3 (3 g) and ammonium formate (2.08 g) in IMS (30 ml) and water (3 ml) was added 5% Pd/C (50% w/w water) (0.25 g). The mixture was heated under a nitrogen atmosphere at 60° C. overnight. The hot reaction mixture was filtered through Dicalite to remove the catalyst. The catalyst was washed with hot IMS (60 ml) and filtered. The filtrates were concentrated under reduced pressure to give the title compound as a white solid (2.34 g).

Method B

2-[3-[(Benzyloxy)imino]-2,4-dioxo-5-phenyl-2,3,4,5-tetrahydro-1H-1,5-benzodiazepinyl)-N-isopropyl-N-phenylacetamide (10 g) was suspended in IMS (100 ml) with 5% Pd/C (50% wet) (1.5 g, 15% w/w) and heated at 70° C. for ~6 hr under a hydrogen atmosphere at 5 bar pressure. The mixture was cooled and THF (50 ml) was added. The mixture was heated to reflux for 2 hours and filtered hot under nitrogen to remove the catalyst. The mixture was concentrated by distillation to ~50 ml with precipitation of the product. The solid is isolated by filtration and washed with IMS (10 ml) and dried in vacuo at 55° C. to yield the title compound as a white solid (7.0 g).

$^1$H NMR (500 MHz, d$_5$-DMSO+D$_2$O) δ0.9 (m, 6H), 4.15 (d, J=12 Hz, 1H), 4.4 (m, 1H), 4.7 (m, 1H), 4.9 (s, 1H), 6.9 (d, J=5 Hz, 1H), 7.2–7.6 (m, 13H).

What is claimed is:

1. A process for the preparation of the compound of formula (I)

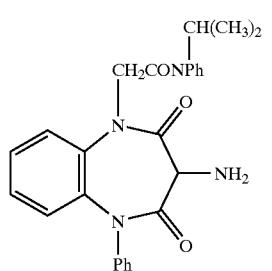

(I)

or an acid addition salt thereof which comprises reacting a compound of formula (II)

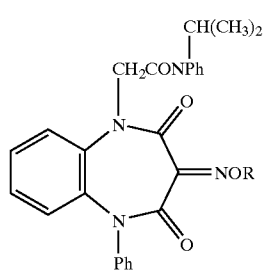

(II)

wherein R is benzyl or a substituted benzyl group under concomitant reduction and hydrogenolysis conditions, followed, if required, by isolation of the compound as an acid addition salt thereof.

2. A process as claimed in claim 1 wherein the concomitant reduction and hydrogenolysis is carried out using a palladium catalyst.

3. A process as claimed in claim 1 wherein the concomitant reduction and hydrogenolysis is carried out using hydrogen or ammonium formate.

4. A process as claimed in any of claims 1 wherein the compound of formula (II) has been prepared by reaction of the ortho phenylene diamine derivative (III) with an activated derivative of the di-acid (IV),

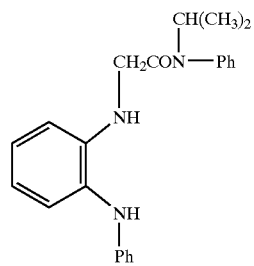

(III)

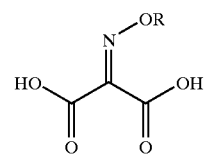

(IV)

wherein R is benzyl or a substituted benzyl group.

5. A process as claimed in claim 4 wherein the activated derivative of the di-acid (IV) is the diacylchloride.

6. A process as claimed in claim 1 wherein R is benzyl.

* * * * *